United States Patent
Ramos et al.

(10) Patent No.: US 9,518,667 B2
(45) Date of Patent: Dec. 13, 2016

(54) TUBING CLAMP

(71) Applicant: C. R. Bard, Inc., Murray Hill, NJ (US)

(72) Inventors: Miguel D. Ramos, Taylorsville, UT (US); Daniel B. Blanchard, Bountiful, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 189 days.

(21) Appl. No.: 14/014,171

(22) Filed: Aug. 29, 2013

(65) Prior Publication Data

US 2014/0060655 A1    Mar. 6, 2014

Related U.S. Application Data

(60) Provisional application No. 61/695,186, filed on Aug. 30, 2012.

(51) Int. Cl.
| F16K 7/04 | (2006.01) |
| A61M 5/00 | (2006.01) |
| F16K 7/06 | (2006.01) |
| A61M 39/28 | (2006.01) |

(52) U.S. Cl.
CPC ............... *F16K 7/063* (2013.01); *A61M 39/28* (2013.01); *A61M 39/281* (2013.01); *A61M 39/284* (2013.01); *A61M 39/286* (2013.01); *F16K 7/066* (2013.01); *Y10T 137/0318* (2015.04)

(58) Field of Classification Search
CPC .................................. F16K 7/063; F16K 7/066
USPC .................................... 251/4, 9, 10; 604/250
See application file for complete search history.

(56) References Cited

U.S. PATENT DOCUMENTS

| 2,503,327 A | 4/1950 | Fields |
| D200,729 S | 3/1965 | Coanda et al. |
| 3,357,674 A | 12/1967 | Coanda et al. |
| 3,374,509 A | 3/1968 | Logan et al. |
| 3,698,681 A | 10/1972 | Lacey |
| 3,713,622 A | 1/1973 | Dinger |
| D230,729 S | 3/1974 | Zeddies |
| 3,822,052 A | 7/1974 | Lange |
| 3,847,370 A | 11/1974 | Engelsher |

(Continued)

FOREIGN PATENT DOCUMENTS

| WO | 2013177537 A1 | 11/2013 |
| WO | 2014036325 A2 | 3/2014 |

OTHER PUBLICATIONS

PCT/US13/57399 filed Aug. 29, 2013 International Search Report and Written Opinion dated Feb. 19, 2014.

*Primary Examiner* — Eric Keasel
*Assistant Examiner* — Kelsey Rohman
(74) *Attorney, Agent, or Firm* — Rutan & Tucker, LLP

(57) ABSTRACT

A clamp for selectively compressing a portion of tubing, such as an extension leg of a PICC or other catheter, is disclosed. The clamp is able to be opened or closed with a thumb and finger of a single hand of a user and is slidably attached to the tubing so as to enable its placement as desired along the tube. In one embodiment, the tubing clamp comprises a body including first and second body portions hingedly connected to one another in a clamshell configuration, a latch for releasably latching the first and second body portions together, and at least two tube compression members. The tube compression members cooperate to compress and occlude a portion of tubing passing through the tubing clamp when the first and second body portions are latched to one another.

22 Claims, 9 Drawing Sheets

(56) References Cited

U.S. PATENT DOCUMENTS

| | | | |
|---|---|---|---|
| 3,942,228 A | 3/1976 | Buckman et al. | |
| 4,053,135 A | 10/1977 | Saliaris | |
| 4,235,412 A | 11/1980 | Rath et al. | |
| 4,248,401 A | 2/1981 | Mittleman | |
| 4,266,751 A | 5/1981 | Akhavi | |
| 4,340,148 A | 7/1982 | Beckham | |
| 4,343,066 A | 8/1982 | Lance | |
| 4,346,869 A | 8/1982 | MacNeill | |
| D268,871 S | 5/1983 | Benham et al. | |
| D271,851 S | 12/1983 | Lance | |
| 4,434,963 A | 3/1984 | Russell | |
| 4,453,295 A | 6/1984 | Laszczower | |
| D279,314 S | 6/1985 | Ishida et al. | |
| 4,560,378 A | 12/1985 | Weiland | |
| 4,588,160 A | 5/1986 | Flynn et al. | |
| 4,589,626 A | 5/1986 | Kurtz et al. | |
| 4,623,102 A | 11/1986 | Hough, Jr. | |
| 4,643,389 A | 2/1987 | Elson et al. | |
| 4,673,161 A | 6/1987 | Flynn et al. | |
| 4,676,530 A | 6/1987 | Nordgren et al. | |
| D298,216 S | 10/1988 | Eisenberg | |
| 4,802,650 A | 2/1989 | Stricker | |
| D303,013 S | 8/1989 | Konopka | |
| D305,151 S | 12/1989 | Bisha | |
| 4,944,485 A | 7/1990 | Daoud et al. | |
| 5,035,399 A | 7/1991 | Rantanen-Lee | |
| 5,083,741 A | 1/1992 | Sancoff | |
| D325,631 S | 4/1992 | Daoud et al. | |
| 5,203,056 A | 4/1993 | Funk et al. | |
| 5,238,218 A | 8/1993 | Mackal | |
| 5,290,239 A | 3/1994 | Classey et al. | |
| D376,974 S | 12/1996 | Chen | |
| 5,591,143 A | 1/1997 | Trombley, III et al. | |
| 5,865,813 A * | 2/1999 | DeKalb et al. | 604/250 |
| 5,951,519 A | 9/1999 | Utterberg | |
| 5,954,657 A | 9/1999 | Rados | |
| 5,967,484 A | 10/1999 | Morris | |
| D427,307 S | 6/2000 | Guala et al. | |
| 6,089,527 A | 7/2000 | Utterberg | |
| 6,101,684 A | 8/2000 | Ginocchio | |
| 6,113,062 A | 9/2000 | Schnell et al. | |
| D431,650 S | 10/2000 | Guala et al. | |
| 6,161,812 A | 12/2000 | Guala et al. | |
| 6,196,519 B1 | 3/2001 | Utterberg | |
| 6,234,448 B1 | 5/2001 | Porat | |
| 6,387,076 B1 * | 5/2002 | Landuyt | A61M 25/02 128/DIG. 6 |
| 6,491,681 B1 | 12/2002 | Kunis et al. | |
| 6,644,618 B1 | 11/2003 | Balbo | |
| 6,742,760 B2 | 6/2004 | Blickhan et al. | |
| 6,840,492 B1 | 1/2005 | Boyne-Aitken | |
| D517,209 S | 3/2006 | Burton et al. | |
| 7,234,677 B2 | 6/2007 | Zerfas | |
| 7,350,761 B1 * | 4/2008 | Stuart | F16K 7/063 251/10 |
| 7,686,279 B2 | 3/2010 | Nerbonne et al. | |
| 7,712,237 B2 | 5/2010 | Wortley et al. | |
| D619,711 S | 7/2010 | Lombardo et al. | |
| 7,758,552 B2 | 7/2010 | Zoltan et al. | |
| D625,003 S | 10/2010 | Stephens | |
| D625,004 S | 10/2010 | McGrady et al. | |
| D635,255 S | 3/2011 | Travis et al. | |
| D637,712 S | 5/2011 | Chau et al. | |
| D638,932 S | 5/2011 | She et al. | |
| 7,954,210 B2 | 6/2011 | Ruffing | |
| 8,276,875 B2 | 10/2012 | Okiyama | |
| 8,328,763 B2 | 12/2012 | Traversaz | |
| D679,009 S | 3/2013 | Amborn et al. | |
| 8,403,291 B2 | 3/2013 | Howlett et al. | |
| 8,430,128 B2 | 4/2013 | Balteau | |
| 8,474,784 B2 | 7/2013 | Kashmirian et al. | |
| 8,636,719 B2 | 1/2014 | Wentling et al. | |
| 8,647,326 B2 | 2/2014 | Solomon et al. | |
| D701,304 S | 3/2014 | Lair et al. | |
| D702,343 S | 4/2014 | Dale et al. | |
| 2004/0162544 A1 | 8/2004 | Raulerson et al. | |
| 2006/0079849 A1 | 4/2006 | Zoltan et al. | |
| 2008/0051731 A1 * | 2/2008 | Schweikert et al. | 604/250 |
| 2008/0082079 A1 | 4/2008 | Braga et al. | |
| 2010/0106101 A1 * | 4/2010 | Fisher et al. | 604/250 |
| 2011/0208132 A1 * | 8/2011 | Clark | A61M 39/1011 604/257 |
| 2012/0232497 A1 | 9/2012 | Singh | |
| 2012/0316539 A1 | 12/2012 | Villasana | |
| 2013/0066280 A1 | 3/2013 | Wallin | |
| 2013/0310768 A1 | 11/2013 | Ebara et al. | |

* cited by examiner

TUBING CLAMP

CROSS-REFERENCE TO RELATED APPLICATIONS

This application claims the benefit of U.S. Provisional Application No. 61/695,186, filed Aug. 30, 2012, and titled "Tubing Clamp," which is incorporated herein by reference in its entirety.

BRIEF SUMMARY

Briefly summarized, embodiments of the present invention are directed to a clamp for selectively compressing a portion of tubing, such as an extension leg of a PICC or other catheter. The clamp is able to be opened or closed with a thumb and finger of a single hand of a user and is slidably attached to the tubing so as to enable its placement as desired along the tube. Its attachment to the tube also prevents loss of the clamp when it is not being used to clamp the tubing. The clamp includes rounded surfaces that reduce trauma and improve patient comfort over other designs, and further includes sufficient surface area for enabling printing to be included thereon.

In one embodiment, therefore, the tubing clamp comprises a body including first and second body portions hingedly connected to one another in a clamshell configuration, a latch for releasably latching the first and second body portions together, and at least two tube compression members. The tube compression members cooperate to compress and occlude a portion of tubing passing through the tubing clamp when the first and second body portions are latched to one another.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a clamp for selectively compressing a portion of tubing, such as an extension leg of a PICC or other catheter. The clamp is able to be opened or closed with two fingers and is slidably attached to the tubing so as to enable its placement as desired along the tube. Its attachment to the tube also prevents loss of the clamp when it is not being used to clamp the tubing. The clamp includes rounded surfaces that reduce trauma and improve patient comfort over other designs, and further includes sufficient surface area for enabling printing to be included thereon.

Figure 1:
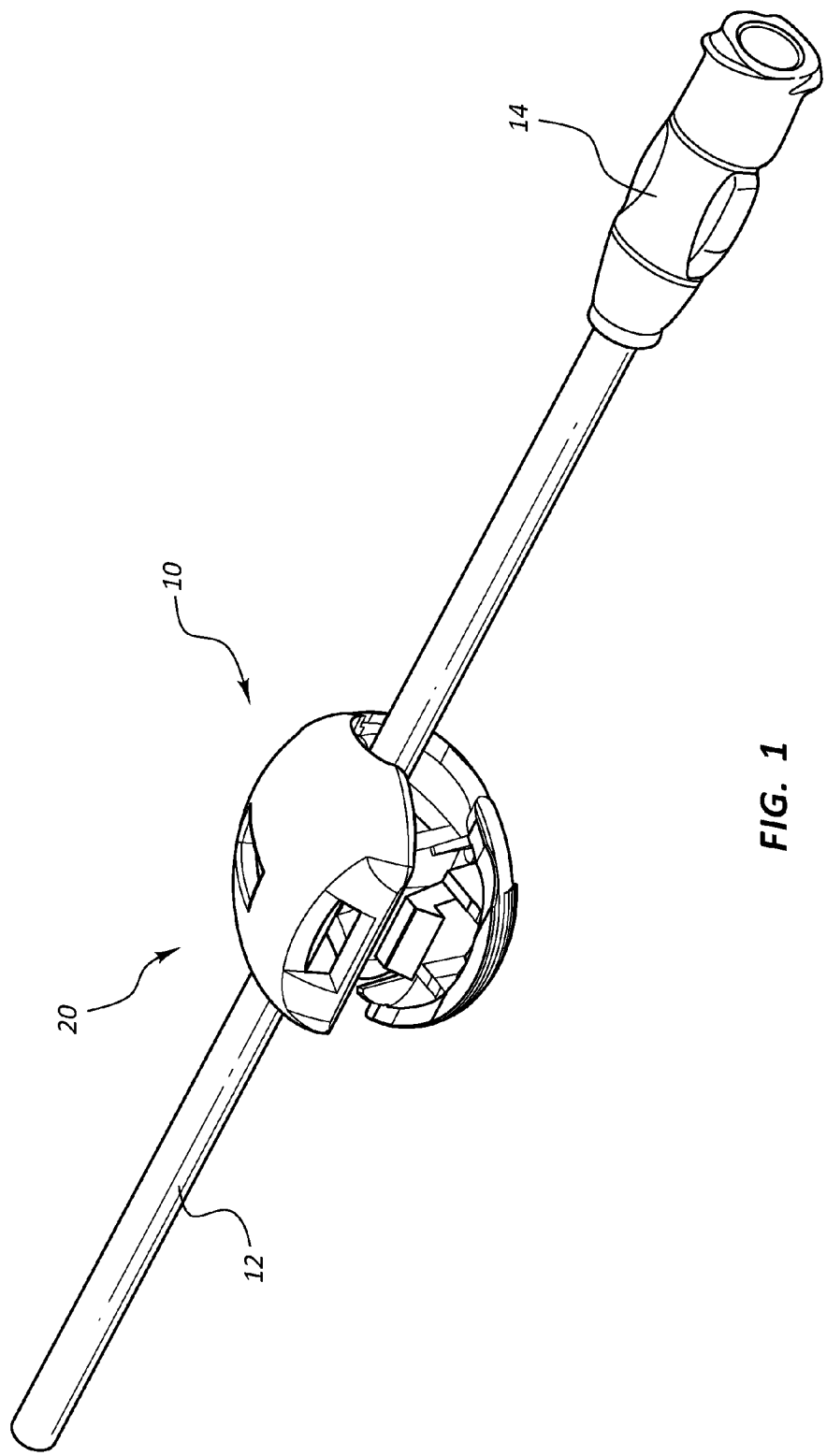
FIG. 1 is a perspective view of a tubing clamp included on an extension leg of a catheter, according to one embodiment.

Reference is first made to FIG. 1, which shows a tubing clamp, generally designated at 10, slidably attached to the tubing of an extension leg 12 and in an unlatched configuration. In the unlatched configuration shown here, the clamp 10 is able to be easily slid along the length of the extension leg 12 so as to enable a user to position it as desired. Note that the extension leg 12 includes a connector 14 and is representative of a wide variety of tubes and tubing, including various catheters and catheter-related tubing, with which a clamp configured in accordance with the present disclosure can be utilized.

Figure 2:
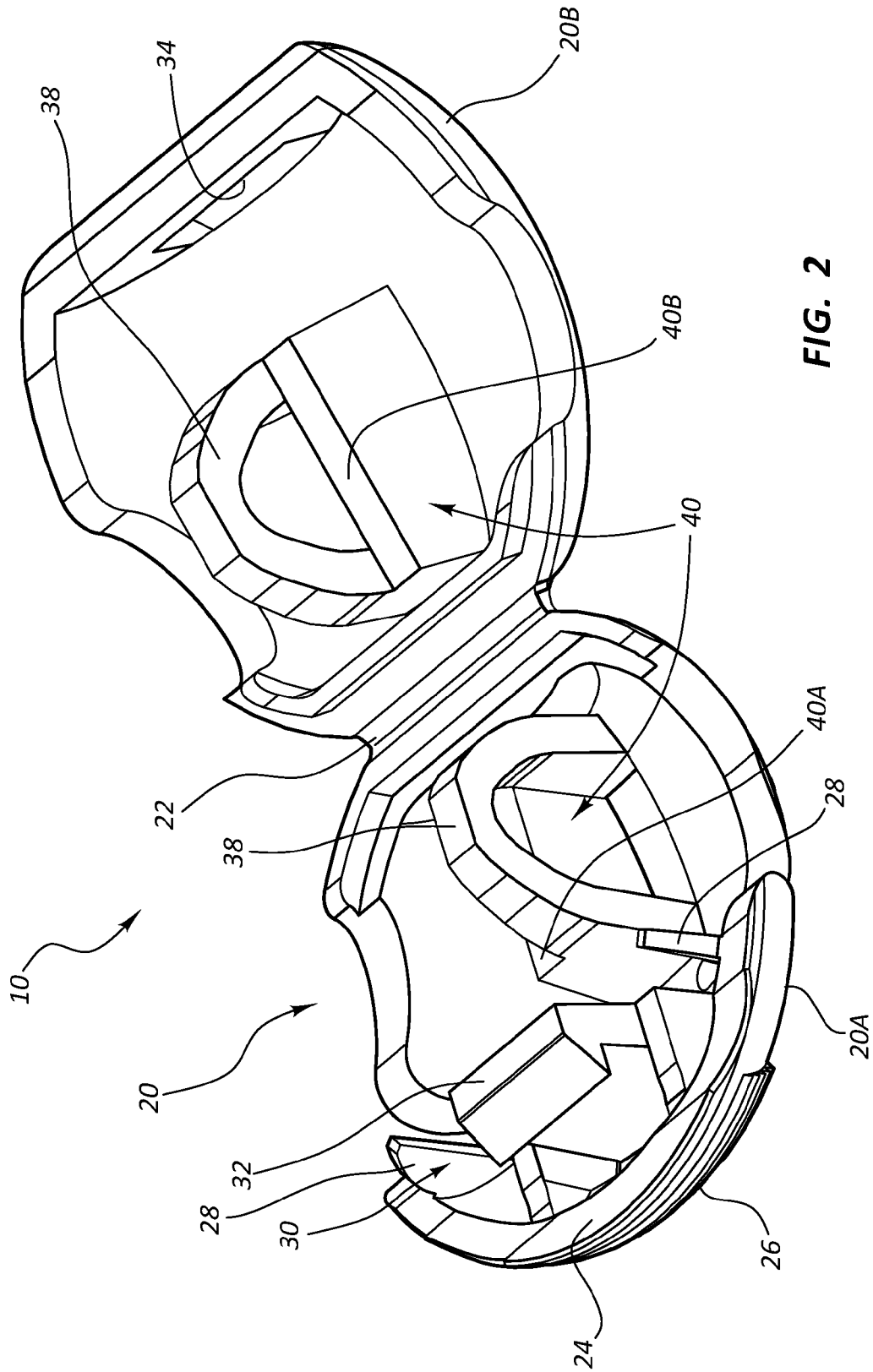
FIG. 2 is a perspective view of the clamp of FIG. 1 in an open configuration.

FIG. 2 shows the clamp 10 in an open configuration, such as during clamp manufacture, in accordance with one embodiment. In detail, FIG. 2 shows various internal components of the clamp 10, including a body 20 defined by a first body portion 20A and a second body portion 20B. The two clamp body portions 20A, 20B are attached to one another via a hinge or other suitable component to enable mutual movement therebetween. In the present embodiment, the clamp body portions 20A, 20B are integrally formed and the hinge is a living hinge 22 integrally formed with the body portions. So configured, the clamp body 20 can be selectively closed and opened, the body having a clamshell-like design.

Figure 3A:
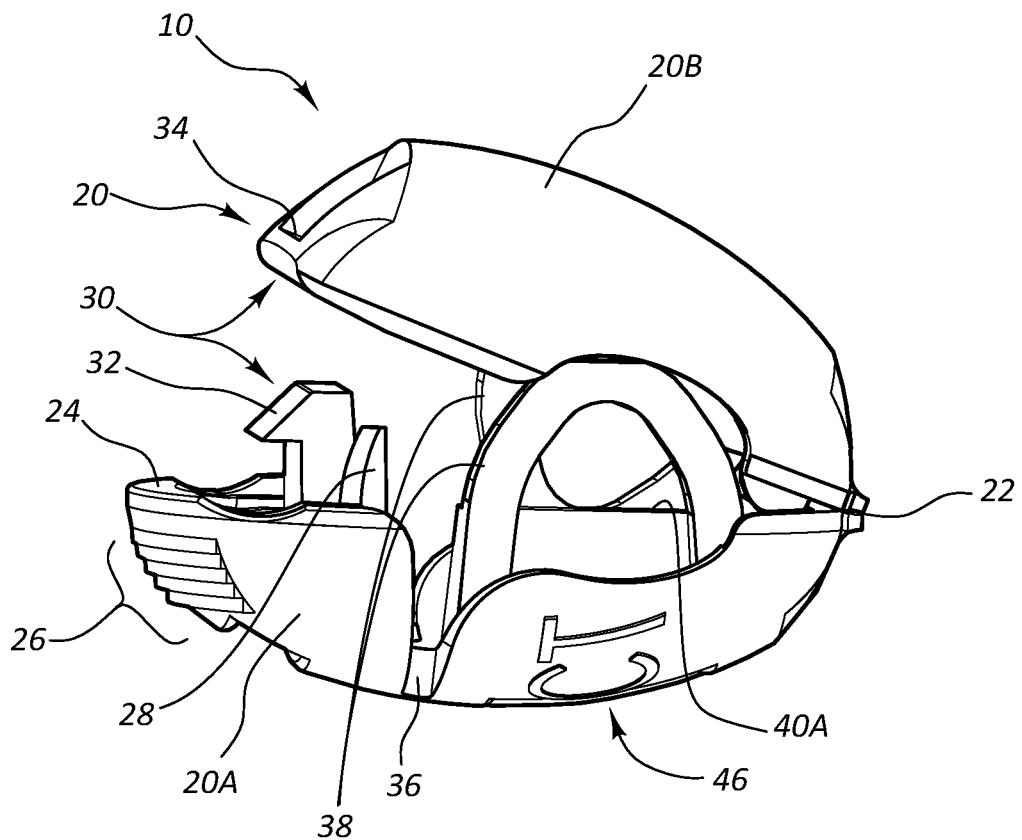
FIGS. 3A-3C are various views of the clamp of FIG. 1 in open and closed configurations.
Figure 3B:
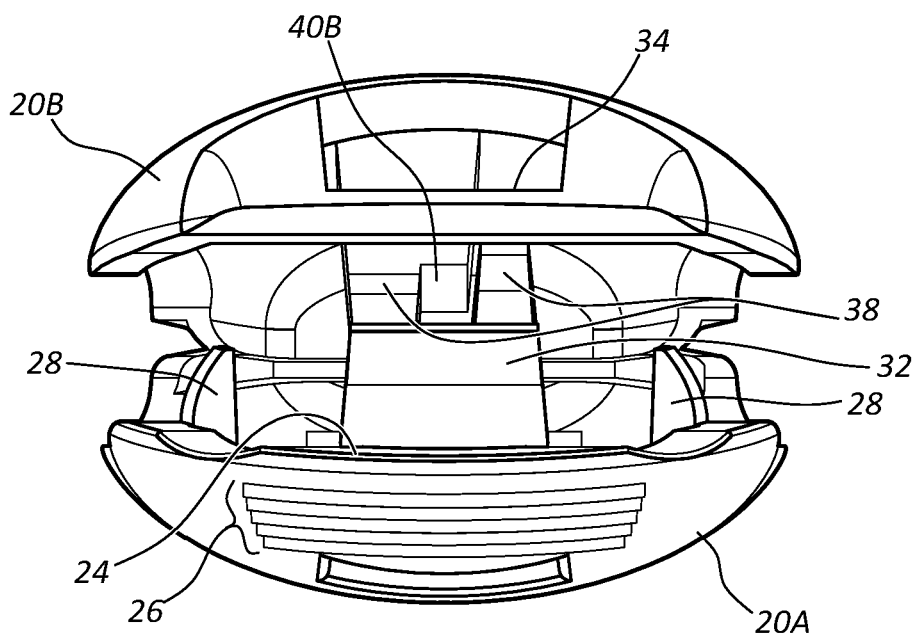
Figure 3C:
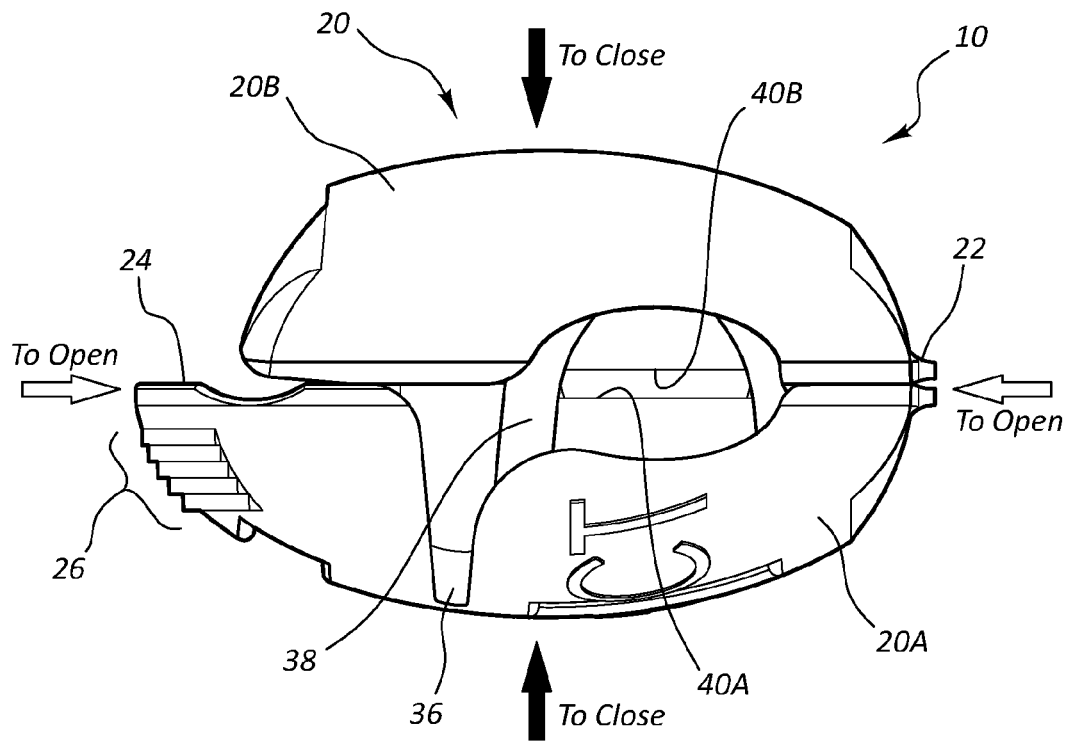

The first body portion 20A defines a lip 24 that protrudes beyond an adjacent portion of the second body portion 20B when the two portions are brought together in the manner shown in FIG. 3C. The lip 24 assists in enabling selective opening of the clamp 10, as will be seen. Gripping surfaces 26 or other suitable surface features are included proximate the lip 24 to assist with finger gripping of the lip and clamp body 20.

Figure 4:
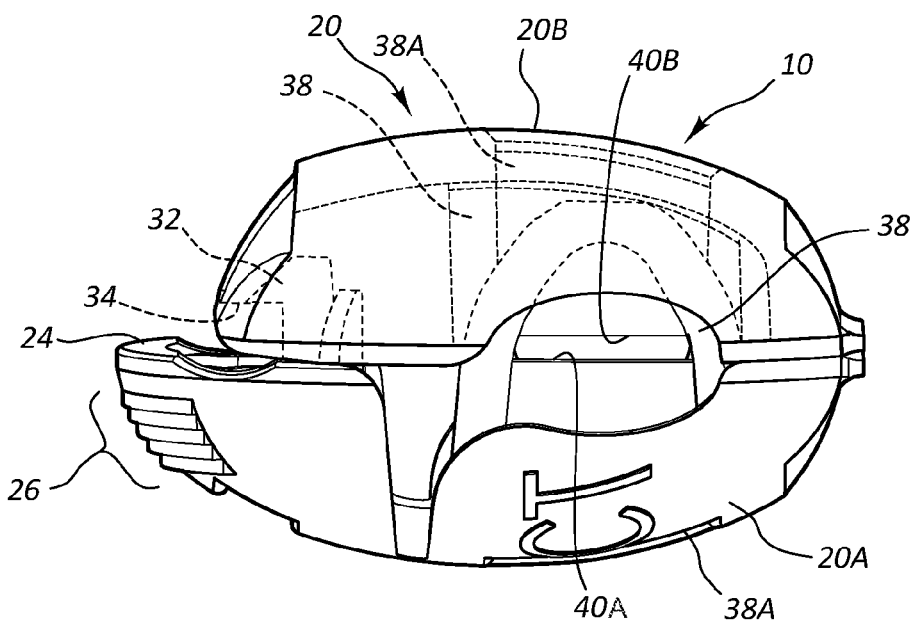
FIG. 4 is an enlarged, partially transparent side view of the clamp of FIG. 1 in a closed configuration.

A latch 30 is included on the clamp 10 to enable selective latching of the first and second body portions 20A, 20B together to close the clamp. As seen in FIG. 2, the latch 30 of the present embodiment includes a male latch portion 32 disposed on the first body portion 20A and a female latch portion 34 disposed on the second body portion 20B. The two latch portions 32 and 34 are cooperatively positioned and configured to releasably latch together via locking insertion of the male latch portion into the female latch portion when the two clamp body portions 20A and 20B are pressed together by the user, as seen in FIGS. 3C and 4. FIG. 4 particularly shows the manner of engagement of the male latch portion 32 with the female latch portion 34 when the clamp 10 is closed. Such engagement by the latch 30 enables the clamp 10 to occlude the tubing on which the clamp is included, as will be seen. It is appreciated that a variety of latching systems and configurations can be employed in addition to that shown and described herein.

Figure 5A:
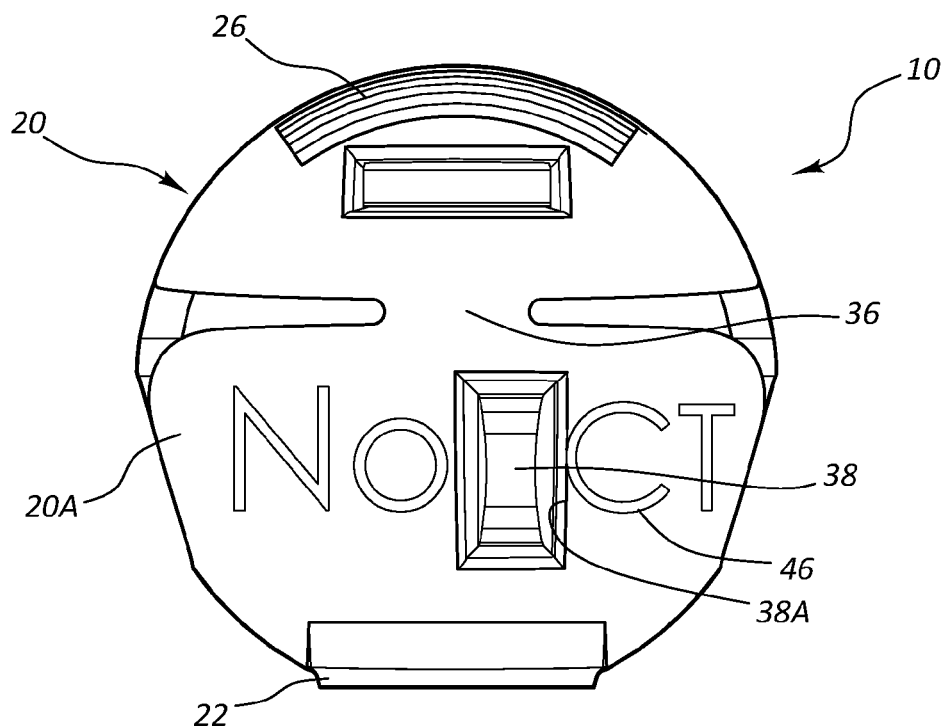
FIGS. 5A and 5B are top and bottom views of the clamp of FIG. 1.

FIGS. 4 and 5A further show that the first body portion 20A includes a compliant segment 36 that enables the lip 24 and portion of the first body portion on which the male latch portion 32 is disposed to flex with respect to the remainder portion of the first body portion. As will be seen, this assists in engagement and disengagement of the latch 30. As best seen in FIGS. 4 and 5A, the compliant segment 36 includes a region of reduced cross-sectional area with respect to adjacent portions of the first body portion 20A. Note that the first and second body portions 20A and 20B in the present embodiment include a thermoplastic or other suitable material such that the compliant portion 36 is able to resiliently bend as described herein. Note that the design, shape, cross-sectional area, and configuration of the compliant segment can vary from what is explicitly shown and described herein.

In accordance with the present disclosure, the body of the clamp can include one or more suitable materials, including but not limited to acetyl, polyester ("PES"), polyethylene terephthalate ("PET"), polyethylene ("PE"), high density polyethylene ("HDPE"), polyvinyl chloride ("PVC"), low-density polyethylene ("LDPE"), polypropylene ("PP"), polystyrene ("PS"), high impact polystyrene ("HIPS"), polyamides ("PA"), nylons, acrylonitrile butadiene styrene ("ABS"), polycarbonate ("PC"), polycarbonate/acrylonitrile butadiene styrene ("PC/ABS"), polyurethane ("PU"), polyetheretherketone ("PEEK"), and polytetrafluoroethylene ("PTFE"). Also, note that any of these materials can include additives, such as glass in one embodiment, for improved mechanical properties. In one embodiment, the body of the clamp includes polypropylene.

Figure 5B:
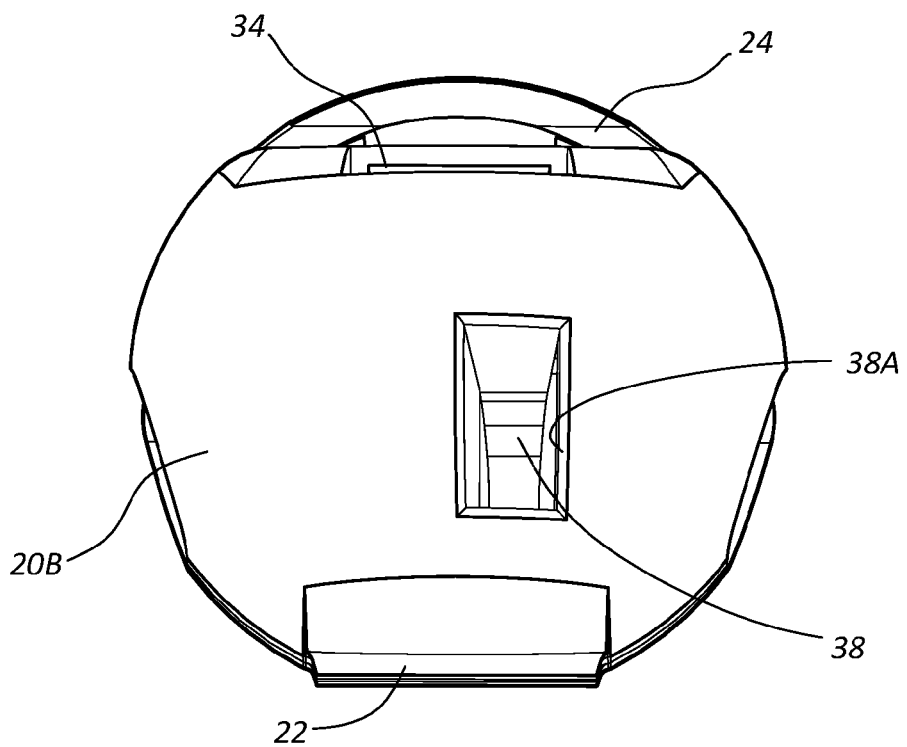

FIGS. 2, 3A, and 4 further illustrate dual tube retention components 38 that are sized and configured to each receive therethrough a portion of the tubing of the extension leg 12 (FIG. 1) or other tubing on which the clamp 10 is disposed. The tube retention components 38 are each included on one of the first and second body portions 20A, 20B such that the clamp 10 is slidably secured to the tubing in the manner shown in FIG. 1 when the clamp is unlatched. This prevents the clamp 10 from opening too widely when unlatched while still enabling the clamp to slide along the tubing. This configuration also prevents unintended separation of the clamp from the extension leg 12. Note that the tube retention components 38 are in linear arrangement with one another when the clamp 10 is latched so as to enable the tubing to pass through the clamp without substantial deviation. The clamp 10 may include extensions 28, which may aid in proper alignment of the components of the clamp 10. FIGS. 5A and 5B show that the retention components 38 are formed in the present embodiment from recesses 38A in each of the first and second body portions 20A, 20B of the clamp body 20. The particular size, shape, number, and placement of the tube retention components can vary.

A set of tube compression members 40 are further included with the clamp 10. In the present embodiment, the tube compression members 40 include a substantially planar first surface 40A included on the first body portion 20A and a substantially planar second surface 40B included on the second body portion 20B. The first and second surfaces 40A, 40B in the illustrated embodiment are disposed adjacent the respective tube retention components 38 and are configured to pinch the tubing between them when the first and second body portions 20A, 20B are latched together in the manner shown in FIGS. 3C and 4. Indeed, FIG. 4 shows the approximate spacing between the first and second tube compression surfaces 40A, 40B, sufficient to compress and occlude the tubing, thus preventing fluid passage therethrough when the clamp 10 is latched. The tube compression members 40 are shown here as flat surfaces that are aligned to converge toward one another when the clamp is latched, though in other embodiments it is appreciated that the members can include other configurations. Note that the spacing between the tube compression surfaces is dependent upon the thickness of the tubing wall. In one embodiment, the spacing between the tube compression surfaces is no greater than twice the tubing wall thickness so as to achieve full occlusion through the tubing. In one embodiment, it is appreciated that the spacing between the tube compression surfaces is slightly less than twice the tubing wall thickness such that both the tubing and the clamp undergo a relatively small amount of deformation when the clamp is latched.

FIGS. 5A and 5B show that in the present embodiment the clamp 10 is of sufficient size as to provide an area for indicia 46 to be included, such as via printing, on the outer surface of the clamp body 20. It is recognized that a variety of alphanumeric, symbolic, iconic or other indicia can be included on the body 20 of the clamp 10 to convey useful information or characteristics regarding the catheter/medical device to which the clamp is attached to the user. Here, for instance, "No CT" is included on the clamp body 20 as the indicia 46, indicating to an observer that the extension leg 12 to which the clamp 10 is attached is not indicated for power injection of fluids therethrough.

As described, FIG. 1 shows the clamp 10 disposed on a portion of the tubing of the extension leg 12 in an unlatched configuration such that the clamp can slide along the length of tubing, the tubing extending through the tube retention components 38 (FIG. 2). To operate the clamp 10, compression is supplied by two or more digits of the user, such as the thumb and forefinger, in the direction indicated by the "to close" arrows in FIG. 3C to cause the male and female latch portions 32, 34 to engage and latch the first and second body portions 20A, 20B together in the closed configuration shown in FIG. 3C and 4. In this configuration the tubing of the extension leg 12 is compressed by the tube compression members, i.e., the first and second tube compression surfaces 40A and 40B, a sufficient amount to desirably prevent fluid passage through the tubing. When clamping of the tubing is no longer desired, pressure by two or more digits, such as the thumb and forefinger, is applied to the clamp 10 in the direction indicated by the "to open" arrows in FIG. 3C, which causes the lip 24 and adjacent portion of the first body portion 20A to push inward and upward, when viewed from the perspective shown in FIG. 3. Again, this movement of the lip 24 and adjacent portion is enabled via the compliant segment 36 (FIGS. 4, 5A). This movement causes disengagement of the male latch portion 32 from the female latch portion 34 and enables the second body portion 40B to hingedly rotate away from the first body portion 40A. This rotation is assisted by the upward movement of the lip 24 and adjacent portions of the first body portion 20A, which can contact the second body portion 20B and urge the two body portions 20A, 20B apart. Separation of the two clamp body portions 20A, 20B also separates the tube compression surfaces 40A, 40B from one another, which ceases compression and occlusion of the tubing of the extension leg 12, thus enabling fluid to flow therethrough. Passage of the tubing through the retention components 38 desirably prevents excessive opening of the clamp body 20 after unlatching occurs.

Figure 6A:
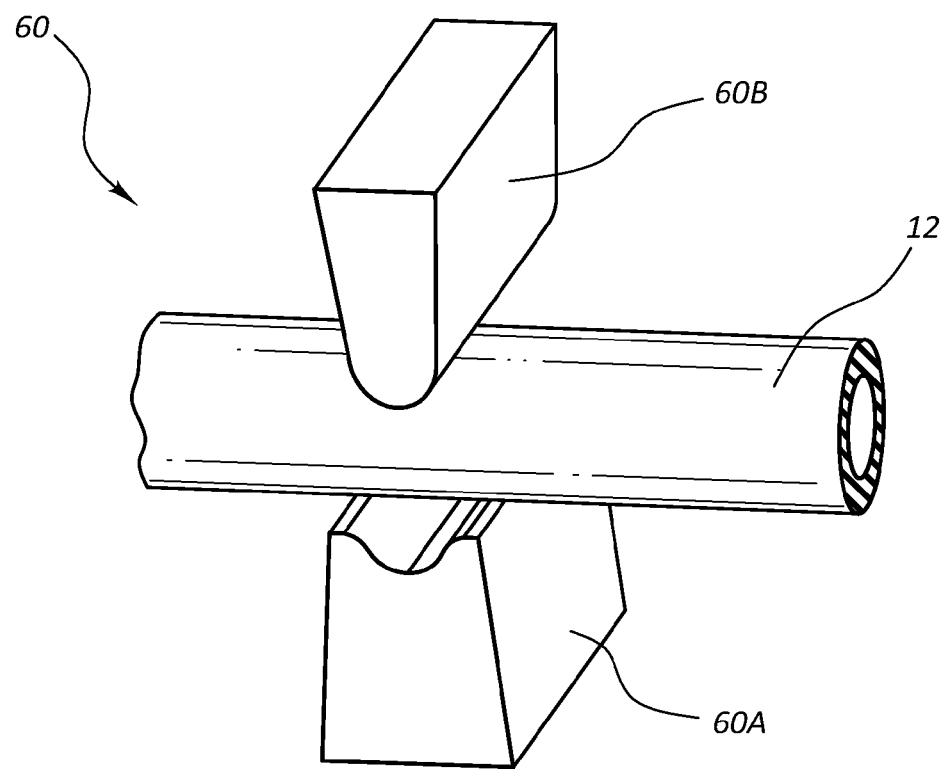
FIGS. 6A and 6B show details of tube compression members for the clamp of FIG. 1 according to one embodiment.
Figure 6B:
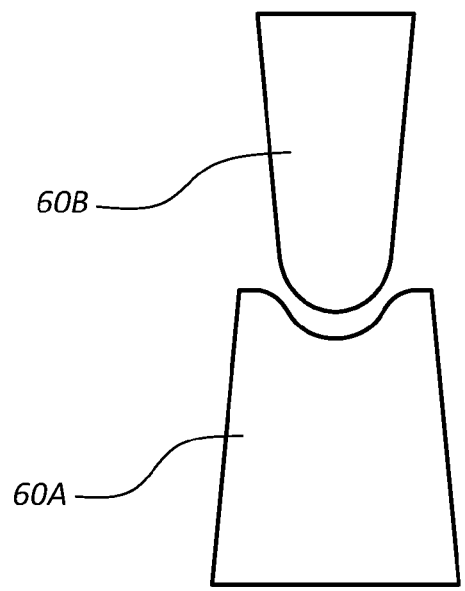

As noted above, the tube compression members can vary from what is shown and described in connection with FIGS. 2-4. FIGS. 6A and 6B show one example of an optional set of tube compression members 60, including a concavely-shaped first compression surface 60A and a correspondingly convexly-shaped second compression surface 60B configured to compress between them the tubing 12 when the clamp 10 is latched together in the manner shown in FIGS. 4 and 5A. Thus, these and other tube compression member designs are contemplated.

Figure 7A:
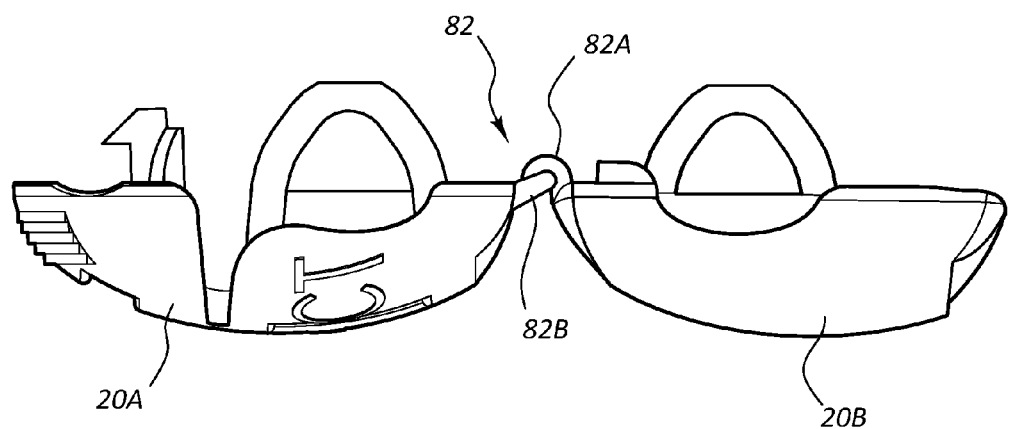
FIGS. 7A and 7B show details of a hinge configuration for a tubing clamp according to one embodiment.
Figure 7B:
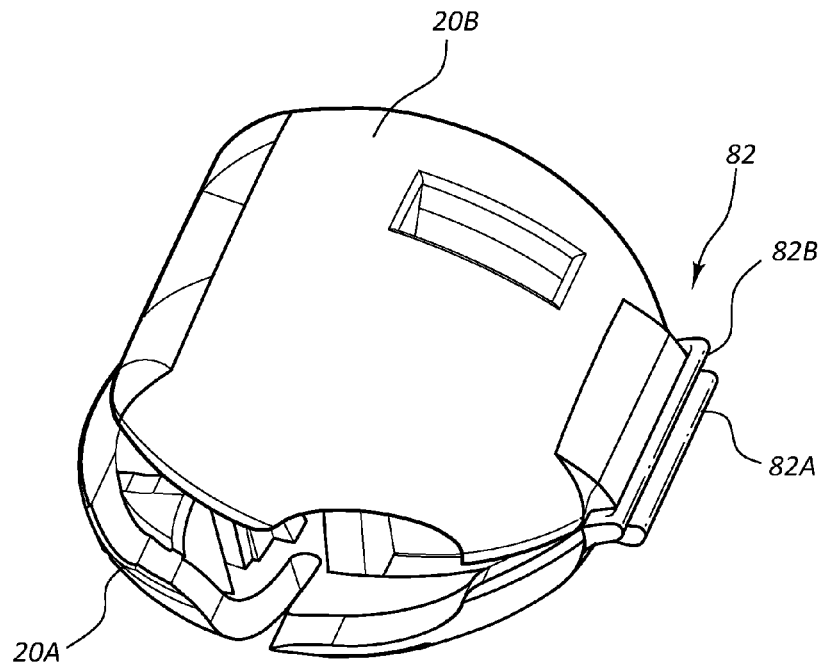

FIGS. 7A and 7B show various details regarding an optional connective scheme 82 for hingedly connecting the first body portion 20A to the second body portion 20B, wherein instead of a living hinge as disclosed in the embodiment further above (FIGS. 2-5B), a hook 82A is included on the second body portion 20B and is configured to rotatably engage with a rod 82B defined on the first body portion 20A, thus enabling hinged movement between the two body portions. FIG. 7B shows an unlatched configuration of the clamp, similar to its configuration when a portion of tubing extends therethrough before latching.

Figure 8A:
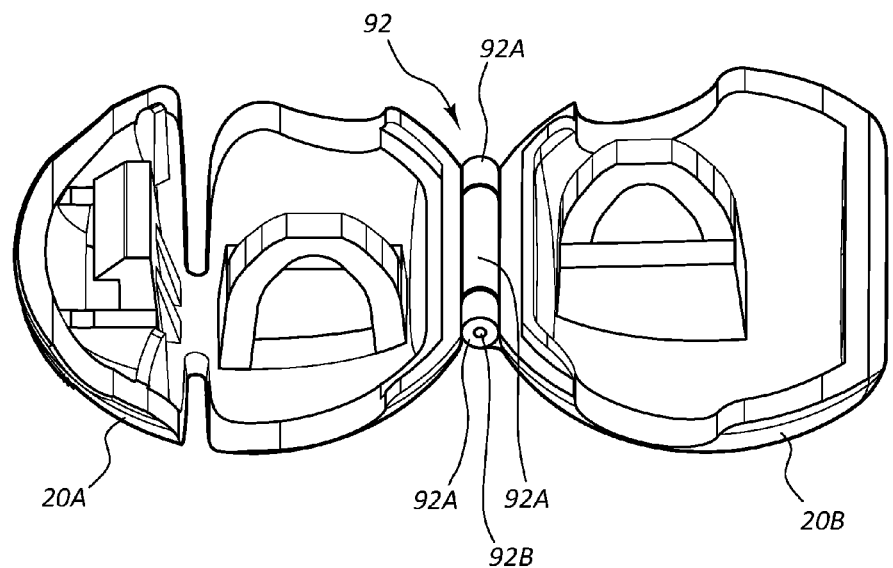
FIGS. 8A and 8B show details of a hinge configuration for a tubing clamp according to one embodiment.
Figure 8B:
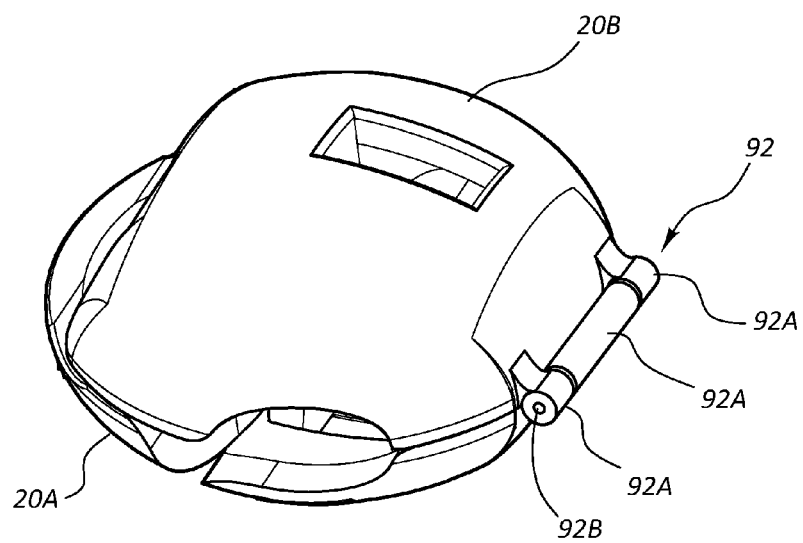

FIGS. 8A and 8B show various details regarding another optional connective scheme for hingedly connecting the first body portion 20A to the second body portion 20B. In particular, a hinge assembly 92 is disclosed, including hinge knuckles 92A defined by both the first and second body portions 20A, 20B and a pin 92B that passes through the hinge knuckles to enable hinged movement of the body portions thereabout. Thus, the first and second body portions 20A, 20B are able to be selectively moved between unlatched and latched configurations. Note that the pin disclosed here can include of any of the materials mentioned above from which the clamp body can be manufactured, as well as medical grade metals, such as stainless steel.

Note that the clamp body 20 can be manufactured in any one of various ways, including injection molding, machining, etc.

Figure 9A:
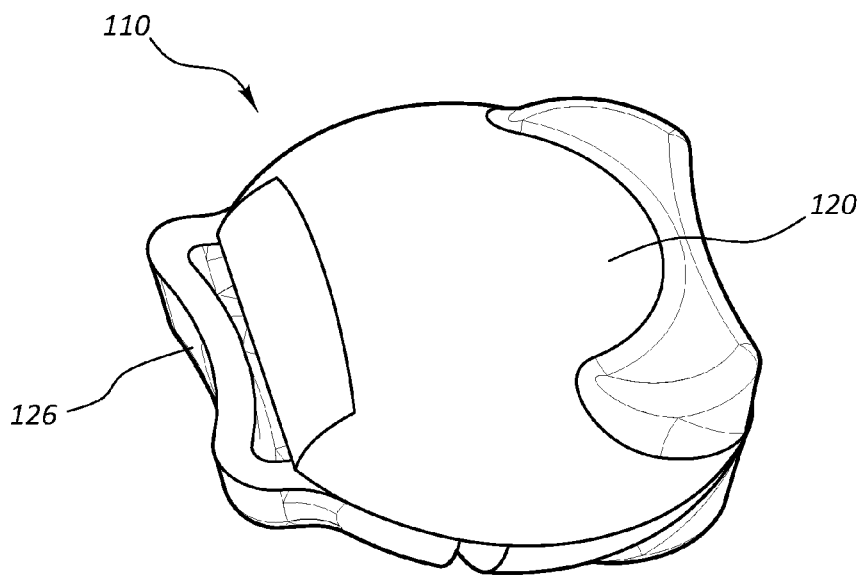
FIGS. 9A and 9B show details of a tubing clamp body according to one embodiment.
Figure 9B:
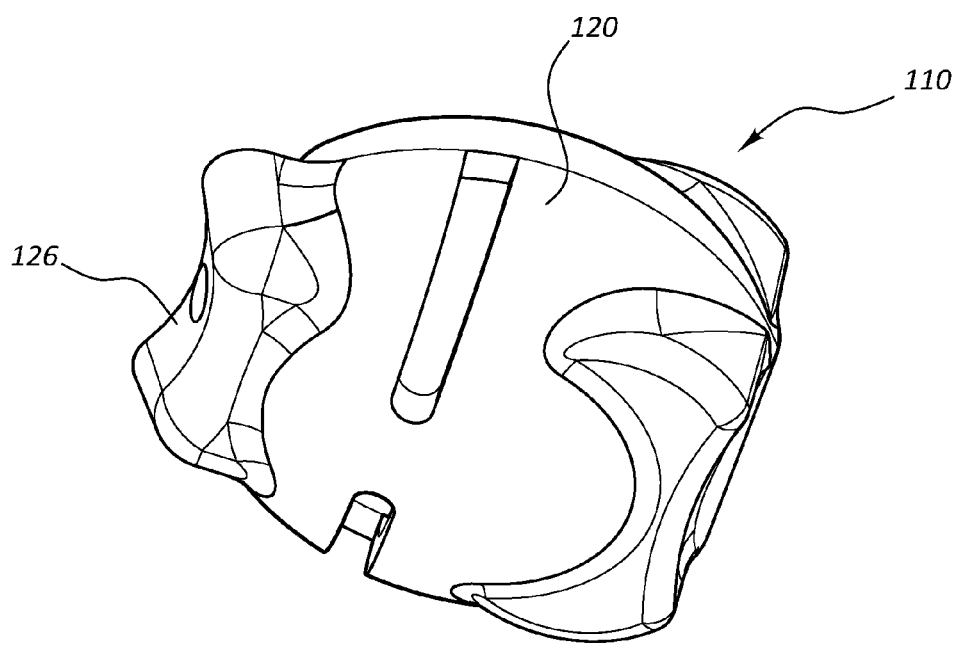

FIGS. 9A and 9B illustrated a tubing clamp 110 having a body 120 and gripping surfaces 126.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A tubing clamp, comprising:
    a body including first and second body portions hingedly connected to one another in a clamshell configuration;
    a latch for releasably latching the first and second body portions together in a closed position, wherein the latch includes a male latch portion and a female latch portion, wherein the male latch portion is included on the first body portion, the first body portion further including a compliant segment that enables a portion of the first body portion on which the male latch portion is disposed to compliantly deform;
    at least two tube compression members that cooperate to compress and occlude a portion of tubing passing through the tubing clamp when the first and second body portions are in the closed position; and
    at least two tube retention members designed to receive the portion of the tubing so as to secure the tubing clamp to the tubing, the at least two tube retention members each comprising a closed loop structure, a first of the at least two tube retention members positioned on the first body portion and a second of the at least two tube retention members positioned on the second body portion, the first and second tube retention members moving in opposite directions around a hinged connection when the first and second body portions move between an open position and the closed position.

2. The tubing clamp as defined in claim 1, wherein the first body portion includes a first tube compression members disposed proximate the first tube retention member.

3. The tubing clamp as defined in claim 1, wherein the at least two tube compression members comprises a first tube compression member and a second tube compression member, each of the first and second tube compression members including a flat surface for engaging a portion of the tubing, the flat surfaces facing one another when the tubing clamp is latched.

4. The tubing clamp as defined in claim 1, wherein the at least two tube compression members comprises a first tube compression member and a second tube compression member, the first and second tube compression members including correspondingly shaped surfaces for engaging a portion of the tubing when the tubing clamp is latched.

5. The tubing clamp as defined in claim 4, wherein the first tube compression member includes a convexly shaped surface and wherein the second tube compression member includes a concavely shaped surface.

6. The tubing clamp as defined in claim 1, wherein the first and second body portions are integrally formed with one another.

7. The tubing clamp as defined in claim 6, wherein a living hinge hingedly connects the first and second body portions.

8. The tubing clamp as defined in claim 1, wherein the compliant segment includes a region of reduced cross-sectional area with respect to adjacent portions of the first body portion.

9. The tubing clamp as defined in claim 1, wherein the first body portion includes a lip disposed proximate to the male latch portion, wherein a user presses proximate the lip during unlatching of the tubing clamp to cause the lip to assist in separating the first body portion from the second body portion.

10. The tubing clamp as defined in claim 9, wherein the first body portion further includes gripping portions disposed proximate to the lip.

11. The tubing clamp as defined in claim 1, wherein a hinge hingedly connects the first and second body portions, the hinge including a hook portion and a rod portion respectively disposed on the first and second body portions.

12. The tubing clamp as defined in claim 1, wherein a hinge hingedly connects the first and second body portions, the hinge including a plurality of knuckles and a pin passing through the knuckles.

13. The tubing clamp as defined in claim 1, wherein the first body portion includes a first of the at least two tube compression members disposed proximate the first tube retention member, wherein the at least two tube retention members each include the closed loop structure designed to receive the portion of tubing passing through the closed loop structure of each of the two tube retention members.

14. A method of using a tubing clamp to selectively occlude a portion of tubing, the method comprising:
grasping a clamp body slidably attached to the portion of tubing, the clamp body including first and second body portions hingedly connected to one another via a hinge in a clamshell-like configuration, a latch for releasably latching the first and second body portions together in a closed position, wherein the latch includes a male latch portion and a female latch portion, wherein the male latch portion is included on the first body portion, the first body portion further including a compliant segment that enables a portion of the first body portion on which the male latch portion is disposed to compliantly deform, at least two tube compression members, and at least two retention members, the at least two retention members encircling the portion of tubing and maintaining the portion of tubing in a substantially parallel orientation to an axis of the hinge; and
selectively latching the first and second body portions together via the latch, wherein the at least two tube compression members of the tubing clamp compress and occlude the portion of tubing when the first and second body portions are in the closed position.

15. The method of using the tubing clamp as defined in claim 14, further comprising selectively unlatching the first and second body portions via the latch, wherein the at least two tube compression members no longer compress and occlude the portion of tubing.

16. The method of using the tubing clamp as defined in claim 15, wherein the selective latching and unlatching of the first and second body portions is performed manually by a thumb and finger of a single hand of a user.

17. A tubing clamp, comprising:
a body including first and second body portions hingedly connected to one another in a clamshell-like configuration, the first and second body portions each having a convex shape and together providing a continuous outer surface over a perimeter thereof in a closed position, the first body portion including a compliant segment;
a latch for releasably latching the first and second body portions together in the closed position, the latch including a male latch portion disposed on the compliant segment of the first body portion and a female latch member on the second body portion;
first and second tube compression members respectively included on the first and second body portions that cooperate to compress a portion of compliant tubing passing through the tubing clamp when the first and second body portions are latched together so as to occlude the passage of fluids through the tubing;
at least two retention members encircling the portion of compliant tubing and maintaining the portion of compliant tubing in a substantially parallel orientation to an axis of a hinge.

18. The tubing clamp as defined in claim 17, further comprising at least one tube retention member that enables the tubing clamp to slide along the portion of compliant tubing when the first and second body portions are unlatched.

19. The tubing clamp as defined in claim 18, wherein the first and second body portions include a thermoplastic and are integrally connected via a living hinge, and wherein the first and second tube compression members each include a flat surface, the flat surfaces aligning when the first and second body portions are latched and cooperating to compress the portion of tubing therebetween.

20. The tubing clamp as defined in claim 19, wherein the compliant segment includes a region of reduced cross-sectional area with respect to adjacent portions of the first body portion that enables compliant deformation of a portion of the first body portion on which the male latch portion is disposed.

21. The tubing clamp as defined in claim 20, wherein the first body portion further includes a protruding lip portion that engages the second body portion during unlatching to urge the second body portion away from the first body portion.

22. The tubing clamp as defined in claim 21, wherein the portion of compliant tubing includes an extension leg of a catheter, and wherein the tubing clamp further includes indicia disposed on an external surface of at least one of the first and second body portions.

\* \* \* \* \*